United States Patent
Foller et al.

[11] Patent Number: 5,882,501
[45] Date of Patent: Mar. 16, 1999

[54] METHOD OF CONVERTING AMINE HYDROHALIDE INTO FREE AMINE

[75] Inventors: Peter C. Foller, Murrysville; David G. Roberts, Gibsonia; Robert H. Tang, Murrysville, all of Pa.

[73] Assignee: PPG Industries, Inc., Pittsburgh, Pa.

[21] Appl. No.: 914,602

[22] Filed: Aug. 18, 1997

[51] Int. Cl.$^6$ ............................ C25B 1/00; C25B 9/00; C25B 7/00
[52] U.S. Cl. ................ 205/551; 204/539; 204/630; 204/632; 204/536
[58] Field of Search .................. 204/541, 539, 204/252, 258, 630, 632, 536; 205/431, 551

[56] References Cited

U.S. PATENT DOCUMENTS

| | | | |
|---|---|---|---|
| Re. 32,398 | 4/1987 | De Witt et al. ............... | 204/72 |
| 596,157 | 12/1897 | Hargreaves ................. | 205/480 |
| 791,194 | 5/1905 | Hoopes ..................... | 205/552 |
| 2,049,467 | 8/1936 | Mnookin .................... | 260/127 |
| 2,209,681 | 7/1940 | Kokatnur et al. ............ | 204/9 |
| 2,737,486 | 3/1956 | Bodamer .................... | 204/72 |
| 2,760,979 | 8/1956 | Burghausen ................. | 260/585 |
| 2,769,841 | 11/1956 | Dylewski et al. ............ | 260/585 |
| 3,183,269 | 5/1965 | Costabello et al. .......... | 260/585 |
| 3,202,713 | 8/1965 | Marullo et al. ............. | 260/583 |
| 3,337,630 | 8/1967 | Moke et al. ................ | 260/583 |
| 3,484,488 | 12/1969 | Lichtenwalter et al. ....... | 260/585 |
| 3,862,234 | 1/1975 | Steele ..................... | 260/585 |
| 4,224,129 | 9/1980 | McIntyre et al. ............ | 204/263 |
| 4,317,704 | 3/1982 | McIntyre et al. ............ | 204/1 R |
| 4,425,202 | 1/1984 | Sullivan ................... | 204/72 |
| 4,481,303 | 11/1984 | McIntyre et al. ............ | 502/159 |
| 4,521,285 | 6/1985 | De Witt et al. ............. | 204/72 |
| 4,561,945 | 12/1985 | Coker et al. ............... | 204/98 |
| 4,582,937 | 4/1986 | Hiraga et al. .............. | 564/498 |
| 4,631,200 | 12/1986 | Bierschenk ................. | 427/113 |
| 4,645,579 | 2/1987 | Weiss et al. ............... | 204/182.4 |
| 4,918,233 | 4/1990 | Deeba et al. ............... | 564/479 |
| 4,980,507 | 12/1990 | Mizui et al. ............... | 564/482 |
| 5,084,148 | 1/1992 | Kazcur et al. .............. | 204/95 |
| 5,208,112 | 5/1993 | Ludwig et al. .............. | 429/20 |
| 5,246,551 | 9/1993 | Pletcher et al. ............ | 204/96 |
| 5,281,311 | 1/1994 | Sharifian et al. ........... | 204/101 |
| 5,290,404 | 3/1994 | Toomey ..................... | 204/72 |
| 5,389,211 | 2/1995 | Sharifian et al. ........... | 204/72 |
| 5,411,641 | 5/1995 | Trainham, III et al. ....... | 204/59 R |

FOREIGN PATENT DOCUMENTS

WO93/00460  1/1993  WIPO.

OTHER PUBLICATIONS

Hydrina® Membrane Electrolyzers Product Brochure, De Nora Permelec S.p.A., Milano, Italy. no month/year available.

Encyclopedia of Chemical Technology, Kirk–Othmer, Fourth Ed., vol. 8, John Wiley & Sons, Inc., New York (1993), pp. 74–108. no month available.

Primary Examiner—Kathryn Gorgos
Assistant Examiner—Edna Wong
Attorney, Agent, or Firm—Irwin M. Stein; James R. Franks

[57] ABSTRACT

Describes a method of electrochemically converting amine hydrohalide, e.g., ethyleneamine hydrochloride, into free amine, e.g., free ethyleneamine, by charging an aqueous solution of amine hydrohalide to the catholyte compartment of an electrolytic cell, which contains a cathode, charging hydrogen gas to the anode compartment of the cell, which contains an anode assembly comprised of a hydrogen consuming gas diffusion anode fixedly held between a current collecting electrode and an anion exchange membrane. The catholyte and anode compartments of the cell are separated by the anion exchange membrane. An amine hydrohalide solution containing free amine is removed from the catholyte compartment.

26 Claims, 4 Drawing Sheets

METHOD OF CONVERTING AMINE HYDROHALIDE INTO FREE AMINE

DESCRIPTION OF THE INVENTION

The present invention relates to a method of electrochemically converting amine hydrohalide into free amine. Particularly, the present invention relates to an electrochemical method of converting ethyleneamine hydrohalides, and more particularly ethyleneamine hydrochlorides, into free ethyleneamines. The present invention also relates to electrolytic cells having a catholyte compartment separated from an anode compartment by an anion exchange membrane, the anode compartment containing an anode assembly.

A major commercial method of producing free amines, particularly free alkyleneamines, and more particularly free ethyleneamines, involves the reaction of a 1,2-dihaloethane, e.g., 1,2-dichloroethane (EDC), with ammonia to produce the entire family of ethyleneamines, including: ethylenediamine (EDA), diethylenetriamine (DETA), triethylenetetramine (TETA), tetraethylenepentamine (TEPA), pentaethylenehexamine (PEHA), piperazine, i.e., diethylenediamine (DEDA), and 2-amino-1-ethylpiperazine. The reaction of EDC and ammonia is well known and is described in U.S. Pat. Nos. 2,049,467, 2,760,979, 2,769,841, 3;183,269, 3,484,488, and 4,980,507.

When the 1,2-dihaloethane reactant is 1,2-dichloroethane, the ethyleneamines are produced as their hydrochloride salts which are subsequently neutralized, typically with an aqueous alkali metal hydroxide, e.g., sodium hydroxide. The neutralization reaction results in the formation of a mixture of free ethyleneamines and by-product alkali metal halide salt, e.g., sodium chloride. The by-product alkali metal halide salt is typically separated from the mixture of free ethyleneamines by an evaporative or distillation process. The mixture of free ethyleneamines is further separated into its individual components by fractional distillation. The presence of halide anion, e.g., chloride anion, in the free ethyleneamines requires that the distillation column(s) be fabricated from expensive corrosion resistant materials such as, titanium and stainless steel. The waste water resulting from the distillation process is typically treated further for the removal of trace amounts of amines prior to disposal. The formation of ethyleneamines from the treatment of ethyleneamine hydrochlorides with an alkali metal hydroxide, e.g., sodium hydroxide, is described in U.S. Pat. Nos. 3,202,713, 3,862,234, 3,337,630, and 4,582,937.

The commercial method described above can be expensive, particularly with regard to the cost of distillation equipment, utility costs, raw material costs, and the required treatment of waste streams. As a result, such a commercial method is typically dedicated to relatively high volume production of free amines, can be expensive to expand, and may not be cost effective for relatively low volume production of free amines.

U.S. Pat. No. 2,737,486 describes an electrolytic process for the conversion of water-soluble acid salts of amines to free amines in an electrolysis cell which contains an anionic permselective membrane between the anode and the cathode. U.S. Pat. No. 5,281,311 describes a process for reducing the acid content of hydroxylamine salt solutions and for preparing hydroxylamines from hydroxylamine salts. The process of U.S. Pat. No. 5,281,311 comprises use in part of an electrolysis cell comprising an anolyte compartment containing an anode, a catholyte compartment containing an oxygen-consuming cathode, and an anionic membrane divider separating said compartments.

The use of either of the processes described in U.S. Pat. Nos. 2,737,486 and 5,281,311 for the conversion of amine hydrohalide to free amine would, in the case of amine hydrochloride, result in the formation of diatomic chlorine ($Cl_2$) within the anode compartment. The formation of $Cl_2$ within the anode compartment would result in degradation of the anion exchange membrane as a result of it being attacked by such $Cl_2$.

International patent publication WO 93/00460 describes an apparatus and process for electrochemically decomposing salt solutions to form the relevant base and acid, and relates to an electrolyzer comprising at least one elementary cell equipped with a novel hydrogen-depolarized anode assembly. The hydrogen depolarized anode assembly comprises a cation-exchange membrane, an electrocatalytic sheet and a rigid current collector which provides a multiplicity of contact points with the electrocatalytic sheet.

Because of the drawbacks of current commercial methods, alternative methods for producing free amines, e.g., free ethyleneamines, that are lower in cost with regard to capital investment for equipment, raw material costs, and costs for the treatment of waste streams are continually being sought.

It has now been discovered that amine hydrohalides can be electrochemically converted to free amines by a method comprising utilizing a two compartment electrolytic cell having the anode and catholyte compartments separated by an anion exchange membrane; circulating hydrogen gas through the anolyte compartment; and providing an anode assembly within the anode compartment, which anode assembly is comprised of either (a) a hydrogen consuming gas diffusion anode fixedly held between the anion exchange membrane and a current collecting electrode or (b) an anion exchange membrane, a current collecting electrode and a bed of porous catalytic particles. The foregoing electrolytic cell configurations have been found to allow the conversion of amine hydrohalides, in particular ethyleneamine hydrochlorides, into free amines without the formation of diatomic halide, in particular diatomic chlorine ($Cl_2$), which can attack and degrade the anion exchange membrane.

In accordance with an embodiment of the present invention, there is provided a method of converting amine hydrohalide into free amine comprising:

(a) providing an electrolytic cell having a catholyte compartment containing a cathode; and an anode compartment containing an anode assembly, said anode assembly comprising a hydrogen consuming gas diffusion anode fixedly held between a current collecting electrode and an anion exchange membrane; the catholyte and anode compartments being separated by the anion exchange membrane;

(b) introducing an aqueous solution of amine hydrohalide into the catholyte compartment;

(c) introducing hydrogen gas into the anode compartment;

(d) passing direct current through the electrolytic cell; and (e) removing an aqueous solution comprising free amine from the catholyte compartment.

In accordance with another embodiment of the present invention, there is provided a method of converting amine hydrohalide into free amine comprising:

(a) providing an electrolytic cell having a catholyte compartment containing a cathode; and an anode compartment containing an anode assembly, said anode assembly comprising an anion exchange membrane, a current collecting electrode, and a bed of porous catalytic particles; the catholyte and anode compartments being separated by the anion exchange membrane;

(b) introducing an aqueous solution of amine hydrohalide into the catholyte compartment;

(c) introducing a hydrogen gas-containing aqueous solution into the anode compartment;

(d) passing direct current through the electrolytic cell; and (d) removing an aqueous solution comprising free amine from the catholyte compartment.

In accordance with a further embodiment of the present invention there is provided an electrolytic cell comprising: a catholyte compartment containing a cathode; and an anode compartment containing an anode assembly, said anode assembly comprising a hydrogen consuming gas diffusion anode fixedly held between a current collecting electrode and an anion exchange membrane; said catholyte and anode compartments being separated by the anion exchange membrane.

In accordance with another further embodiment of the present invention there is provided an electrolytic cell comprising: a catholyte compartment containing a cathode; and an anode compartment containing an anode assembly, said anode assembly comprising an anion exchange membrane, a current collecting electrode, and a bed of porous catalytic particles; said catholyte and anode compartments being separated by the anion exchange membrane.

The features that characterize the present invention are pointed out with particularity in the claims which are annexed to and form a part of this disclosure. These and other features of the invention, its operating advantages and the specific objects obtained by its use will be more fully understood from the following detailed description and the accompanying drawings in which preferred embodiments of the invention are illustrated and described.

Other than in the operating examples, or where otherwise indicated, all numbers expressing quantities of ingredients or reaction conditions used in the specification and claims are to be understood as modified in all instances by the term "about."

BRIEF DESCRIPTION OF THE DRAWINGS

In FIGS. 1–4, like reference numerals represent the same structural parts, the same solutions and the same conduits.

DETAILED DESCRIPTION OF THE INVENTION

Figure 1:
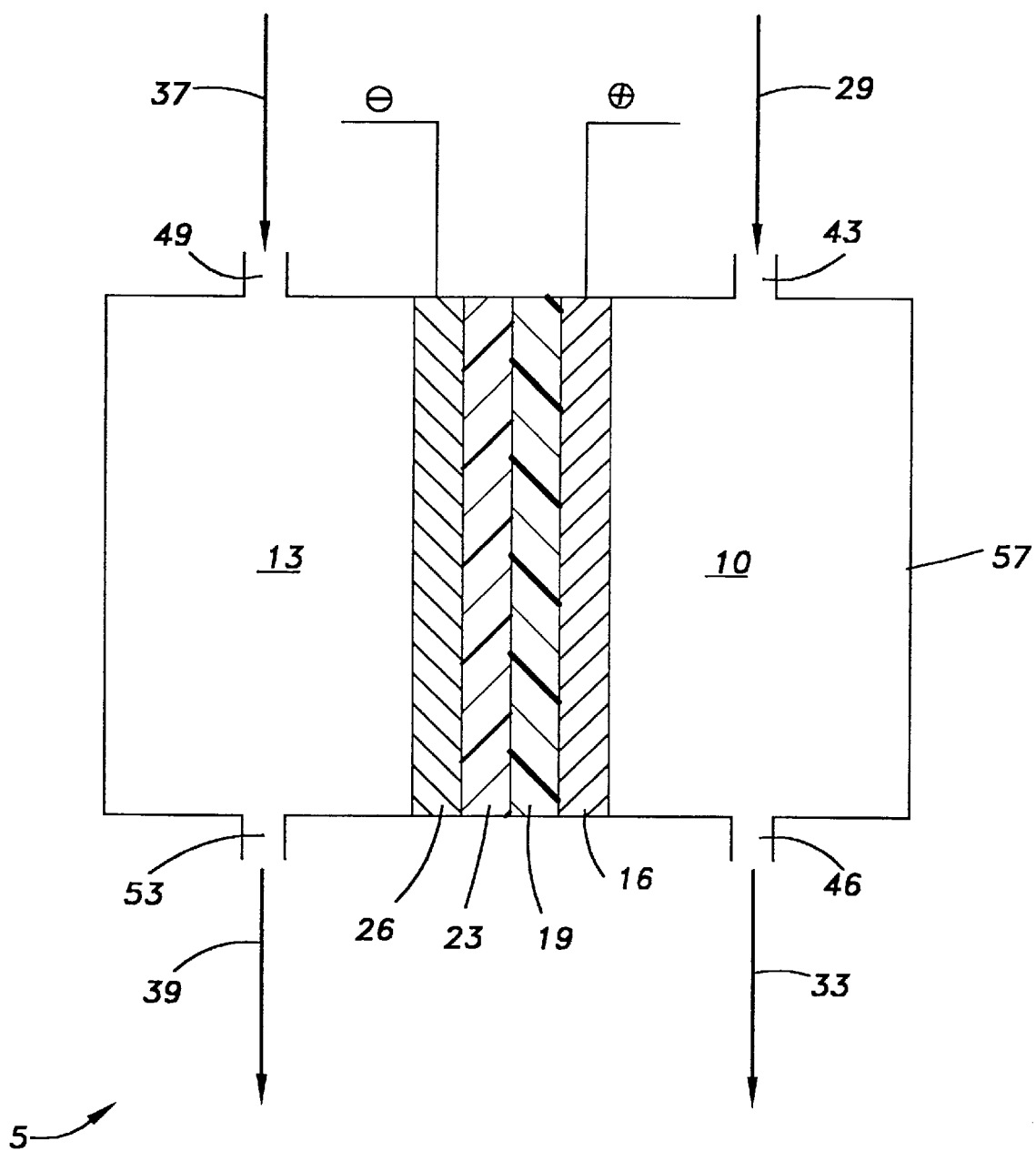
FIG. 1 is a schematic representation of an electrolytic cell useful for converting amine hydrohalide into free amine in accordance with an embodiment of the method of the present invention.

In the practice of the present invention, electrolytic cells, such as those represented in FIGS. 1 through 4, are provided for the conversion of amine hydrohalide into free amine. Referring now to FIG. 1, electrolytic cell 5 comprises a housing 57 having therein a catholyte compartment 13 and an anode compartment 10. The catholyte compartment 13 has an inlet 49 and an outlet 53, and also has therein a cathode 26. The anode compartment has an inlet 43 and an outlet 46, and also has therein an anode assembly comprised of a hydrogen consuming gas diffusion anode 19, which is fixedly held between a current collecting electrode 16 and an anion exchange membrane 23. The catholyte and anode compartments are separated by the anion exchange membrane 23, more particularly, the anode assembly. The cathode 26 and the current collecting electrode 16 are connected to an external power source, not shown.

While cathode 26 is depicted in FIG. 1 as abutting anion exchange membrane 23, it is contemplated that cathode 26 can occupy a position within cathode compartment 13 such that it is not abutting membrane 23. If cathode 26 is not abutting anion exchange membrane 23, an additional means of supporting membrane 23 may be present within cathode compartment 13, e.g., a nonconductive screen having a mesh-like configuration, not shown, abutting membrane 23 but not abutting cathode 26.

Figure 4:
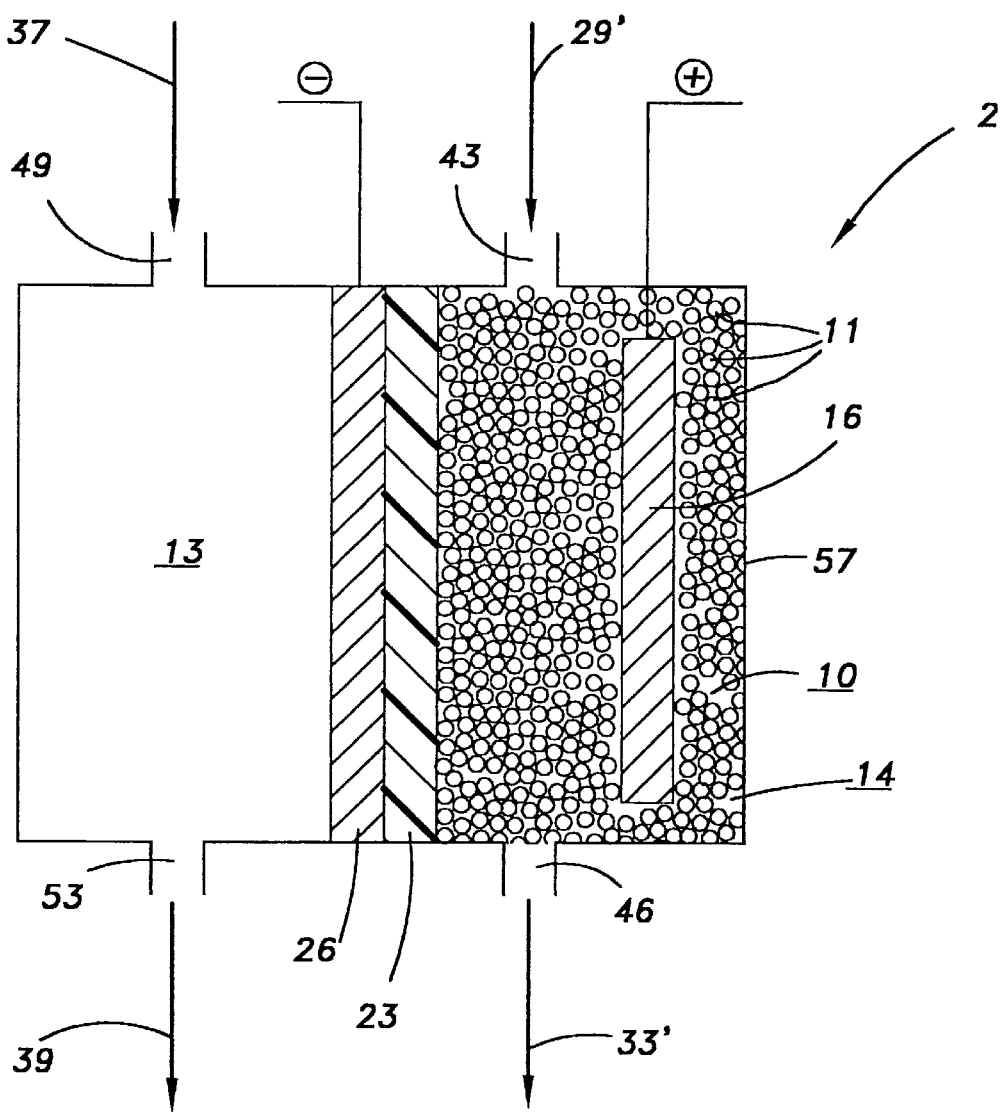
FIG. 4 is a schematic representation of an electrolytic cell useful for converting amine hydrohalide into free amine in accordance with a further embodiment of the method of the present invention wherein the anode compartment contains an anode assembly comprised in part of a bed of porous catalytic particles.

The anode assembly of electrolytic cell 2 of FIG. 4 comprises an anion exchange membrane 23, a bed 14 of porous catalytic particles 11 and a current collecting electrode 16 within bed 14. As is known to those of ordinary skill in the art, the current collecting electrode 16 is spaced from anion exchange membrane 23 to obtain an optimum level of performance, e.g., optimum current density and voltage, for the electrolytic cell. The precise position of current collecting electrode 16 relative to anion exchange membrane 23 is typically determined readily by experimentation.

Electrolytic cells 5 and 2 may be assembled by any appropriate method as long as the basic structural configuration depicted in FIGS. 1 and 4 is retained. For example, the catholyte and anode compartments may each be fabricated separately and then assembled by clamping or otherwise fastening the compartments together.

Housing 57 may be fabricated from any of the known conventional materials for electrolytic cells, or combinations of these known materials, that are preferably at least corrosion resistant to the environment to which the housing is exposed and compatible with the materials comprising the process streams present within or circulated through the catholyte and anode compartments. Examples of materials from which housing 57 may be fabricated include, but are not limited to: metal, e.g., stainless steel, titanium and nickel; plastics, e.g., poly(vinylidenefluoride), polytetrafluoroethylene, which is sold under the trademark "TEFLON" and which is commercially available from E.I. du Pont de Nemours and Company of Wilmington, Del., glass filled polytetrafluoroethylene, polypropylene, polyvinylchloride, chlorinated polyvinylchloride and high density polyethylene. Preferred materials from which housing 57 may be fabricated include: poly(vinylidenefluoride) and stainless steel.

If housing 57 is fabricated from an electrically conductive material, such as stainless steel, then appropriately positioned nonconductive gaskets would typically also be present, as is known to those of ordinary skill in the art. For example, if the compartments of the cell are prefabricated separately from stainless steel, such gaskets would typically be placed between those portions of the prefabricated compartments that would otherwise abut each other upon assemblage of the electrolytic cell. Such nonconductive gaskets may be fabricated from synthetic polymeric materials, e.g., copolymers of ethylene and propylene, and fluorinated polymers.

Cathode 26 and current collecting electrode 16 each may be fabricated from any appropriate material that is at least both corrosion resistant to the environments to which they are exposed and electrically conductive. In electrolytic cell 5, it is also desirable that current collecting electrode 26 be substantially rigid so as to provide a support for hydrogen consuming gas diffusion anode 19 and anion exchange membrane 23. Materials from which cathode 26 and current collecting electrode 16 may be fabricated include, but are not limited to: graphite; platinum; titanium coated with platinum; titanium coated with an oxide of ruthenium; nickel; stainless steel; specialty steels including high alloy steels containing nickel, chromium, and molybdenum, e.g., HASTELLOY® C-2000™ alloy and HASTELLOY® C-276™ alloy from Haynes International, Inc. While current collecting electrode 16 may be fabricated from stainless steel, it is preferred to use a more corrosion resistant material such as a high alloy steel, e.g., HASTELLOY® C-2000™ alloy. Cathode 26 and current collecting electrode 16 are each preferably comprised of a material selected from the group consisting of graphite, platinum, titanium coated with platinum, titanium coated with an oxide of ruthenium, nickel, stainless steel, high alloy steel, and appropriate combinations of such materials.

Preferably, both cathode 26 and current collecting electrode 16 have a perforated or mesh-like configuration. A perforated or mesh-like configuration provides for increased cathode and electrode surface area, and minimizes interference with the transport of anions across the anion exchange membrane.

Anion exchange membrane 23 used in the practice of the present invention can be prepared from any appropriate material that is permeable to and capable of transferring anions. Typically, such membranes are comprised of commercially available organic polymers, often thermoplastic polymers, containing weakly basic pendant polar groups. The membranes may comprise polymers based on fluorocarbons, polystyrene, polypropylene, polybutadiene, polyisoprene, polyisobutylene, polyethylene and hydrogenated styrene/butadiene block copolymers. For example, one such representative membrane comprises polystyrene which has dialkylamino groups that have been converted into quaternary ammonium ions covalently bonded to at least some of the benzene rings of the polystyrene backbone. It is preferable that the anion exchange membrane also be physically durable and stable towards exposure to acids, in particular hydrogen halides, e.g., hydrogen chloride.

A particular example of an anion exchange membrane used in the practice of the present invention is a copolymer of styrene and divinylbenzene which contains from 4 percent (%) to 16%, typically from 6% to 8%, by weight of divinylbenzene and also quaternary ammonium groups as anion carriers. Such membranes are available commercially under the trade designation RAIPORE® from RAI Research Corporation, and TOSFLEX® from Tosoh Corporation. Other suitable membranes include, but are not limited to: NEOSEPTA® membranes from Tokyuama Soda; SELEMION membranes from Asahi Glass; and IONAC MA 3148, MA 3236 and MA 3457 (based on a polymer of heterogeneous polyvinyl chloride substituted with quaternary ammonium groups) membranes from Ritter-Pfaulder Corporation. Particularly preferred anion exchange membranes are NEOSEPTA® ACM and NEOSEPTA® AHA-2 membranes, available commercially from Tokuyama Soda of Japan, which are described as being comprised of a copolymer of styrene and divinylbenzene having pendent quaternary ammonium groups.

The hydrogen consuming gas diffusion anode 19 of electrolytic cell 5 may be fabricated from any suitable material which provides an electrochemically active catalytic surface upon which hydrogen gas ($H_2$) can be converted to hydrogen cation ($H^+$), through which both hydrogen gas and halide anions may diffuse, and which is also semihydrophobic. By semihydrophobic is meant that an aqueous liquid can penetrate the anode without flooding it, i.e., without preventing the electrochemical conversion of hydrogen gas to hydrogen cation. The electrochemical activity is typically provided by a catalytic material. Examples of suitable catalytic materials include, but are not limited to, platinum, ruthenium, osmium, rhenium, rhodium, iridium, palladium, tungsten carbide, gold, titanium, zirconium, alloys of these with non-noble metals, and appropriate combinations thereof.

The hydrogen consuming gas diffusion anode 19 used in the practice of the present invention is preferably comprised of platinum, e.g., platinum supported on carbon black, preferably hydrophilic carbon black, or finely powdered platinum (platinum black), which has been dispersed in a polymer matrix. Examples of useful polymer matrices include fluorinated and perfluorinated polymers. A preferred polymer in which platinum supported on hydrophilic carbon black may be dispersed is polytetrafluoroethylene. The hydrogen consuming gas diffusion anode 19 may be comprised of from 0.1 milligrams platinum per square centimeter of the hydrogen consuming gas diffusion anode ($mg/cm^2$) to 15 $mg/cm^2$, preferably from 0.5 $mg/cm^2$ to 10 $mg/cm^2$, and more preferably from 0.5 $mg/cm^2$ to 6 $mg/cm^2$.

Gas diffusion anode 19 can be fixedly held between anion exchange membrane 23 and current collecting electrode 16 by any appropriate method known to those of ordinary skill in the art, provided that hydrogen consuming gas diffusion anode 19 has sufficient electrical contact with current collecting electrode 16. Such methods include, but are not limited to: maintaining a higher internal pressure within the catholyte compartment relative to the anode compartment; clamping of components 23, 19 and 16 together; providing a pair of separate biasing elements within each of the catholyte and anode compartments, e.g., a first electrically nonconductive plastic spring, not shown, in biased contact with electrode 16 and the inner wall of anode compartment 10, and a second electrically nonconductive plastic spring, not shown, in biased contact with cathode 26 and the inner wall of catholyte compartment 13; and combinations of these methods.

In one embodiment of the present invention, the hydrogen consuming gas diffusion anode 19 is hot-pressed onto one side of anion exchange membrane 23. In another embodiment of the present invention, the hydrogen consuming gas diffusion anode 19 is simply placed between the anion exchange membrane 23 and the current collecting electrode 16 prior to assembly of electrolytic cell 5. In yet another embodiment of the present invention, carbon cloth or carbon paper, not shown, is placed between hydrogen consuming gas diffusion anode 19 and current collecting electrode 16 to provide additional support to the hydrogen consuming gas diffusion anode. The carbon cloth and carbon paper are both preferably semihydrophobic, e.g., treated with TEFLON® polytetrafluoroethylene prior to use. Optionally, the carbon cloth and carbon paper may also be impregnated with a catalytic material, such as platinum.

Ensuring that electrical contact exists between anode 19 and electrode 16 of electrolytic cell 5 is important in the practice of the present invention. In one embodiment of the present invention, electrical contact is maintained between anode 19 and electrode 16 by ensuring that a positive internal pressure difference exists between the catholyte and anode compartments. By positive internal pressure difference is here meant that the internal pressure of the catholyte compartment is greater than that of the anode compartment. Values of positive internal pressure difference are determined by subtracting the internal pressure of the anode compartment from that of the catholyte compartment.

The upper limit of the positive internal pressure difference between the catholyte and anode compartments will depend on a number of factors including for example, the maximum pressure that the anion exchange membrane can endure before it bursts (burst strength). In the practice of the method of the present invention, the positive internal pressure difference between the catholyte and anode compartments will typically have a minimum value of at least 0.07 Kilograms per square centimeter ($Kg/cm^2$) (1 pound per square inch (psi)), preferably at least 0.14 $Kg/cm^2$ (2 psi), and more preferably at least 0.21 $Kg/cm^2$ (3 psi). The positive internal pressure difference between the catholyte and anode compartments will also typically have a maximum value of less than 1.40 $Kg/cm^2$ (20 psi), preferably less than 0.70 $Kg/cm^2$ (10 psi), and more preferably less than 0.49 $Kg/cm^2$ (7 psi). In the practice of the method of the present invention, the positive internal pressure difference between the catholyte and anode compartments may range between any combination of these minimum and maximum values, inclusive of the recited values.

The catalytic particles of the bed 14 of porous catalytic particles 11 of electrolytic cell 2 of FIG. 4 may be fabricated from any suitable material that provides an electrochemically active, electrically conductive surface upon which hydrogen gas ($H_2$) may be converted to hydrogen cation ($H^+$), and which is also semihydrophobic. By semihydrophobic is meant that an aqueous liquid can penetrate the catalytic particles without flooding them, i.e., without preventing the electrochemical conversion of hydrogen gas to hydrogen cation. It is preferred that the catalytic particle itself be a coated particle having a substrate which is at least partially covered, and preferably substantially covered, with an electrochemically active and electrically conductive coating.

The substrate may be electrically conductive or electrically nonconductive, and chemically inert or chemically active. Substrates which are electrically conductive, chemically inert, and hold their shape are preferred. The substrate may be of any shape or combination of shapes, e.g., irregularly and/or spherically shaped, and of a size smaller than 0.3 mm to as large as or larger than 25 mm. Spherically shaped substrates having a size of from 0.7 mm to 4 mm are generally preferred. The substrate may be a material selected from the group consisting of steel, iron, graphite, nickel, platinum, copper and silver. In a particularly preferred embodiment of the present invention, the substrate is graphite.

The coating on the substrate is an admixture of a binder and an electrochemically active, electrically conductive catalyst, and may be of any convenient thickness, e.g., from 5 to 75 microns. Thicknesses of 25 microns are particularly preferred. The coating may be either porous or nonporous, preferably porous. The binder is preferably a hydrophobic material prepared from a synthetic polymer, examples of which include, but are not limited to: polytetrafluoroethylene; polychlorotrifluoroethylene; polytrifluoroethylene; polyvinylfluoride; poly(vinylidenefluoride); and copolymers including interpolymers and terpolymers prepared from monomers including, tetrafluoroethylene, trifluoroethylene, chlorotrifluoroethylene, vinylidine fluoride and vinyl fluoride monomers. Polytetrafluoroethylene is particularly preferred.

The coating on particles 11 also contains an electrochemically active, electrically conductive catalyst material. Examples of suitable catalyst materials include, but are not limited to, platinum, ruthenium, osmium, rhenium, rhodium, iridium, palladium, tungsten carbide, gold, titanium, zirconium, alloys of these with non-noble metals, and combinations thereof. The catalyst material may also be supported on carbon, preferably carbon black, and more preferably hydrophilic carbon black. A particularly preferred catalyst material is platinum supported on hydrophilic carbon black.

Catalytic particles 11 are preferably comprised of graphite substantially coated with an admixture of polytetrafluoroethylene and platinum supported on carbon black, and in particular, hydrophilic carbon black. Catalytic particles that may be used in the present invention are described also in U.S. Pat. No. 4,481,303, the disclosure of which is incorporated herein by reference in its entirety.

The present invention relates to a method of converting amine hydrohalide into free amine. As used herein, the term "halide" is meant to include chloride, bromide and iodide. Amines that may be prepared from their corresponding amine hydrohalides according to the method of the present invention include, but are not limited to: ammonia; mono alkyl, e.g., $C_1$–$C_{12}$ alkyl, amines, di- and tri-substituted alkyl, e.g., $C_1$–$C_{12}$ alkyl, amines, in which the alkyl groups may be the same or different, saturated or unsaturated, examples of saturated alkyl groups include, but are not limited to, methyl, ethyl, isopropyl, n-butyl, tert-butyl, amyl and dodecyl, examples of unsaturated alkyl groups, include, but are not limited to, allyl and methallyl; one or more amines belonging to the family of ethyleneamines, including, ethylenediamine (EDA), diethylenetriamine (DETA), triethylenetetramine (TETA), tetraethylenepentamine (TEPA), pentaethylenehexamine (PEHA), piperazine (DEDA), and 2-amino-1-ethylpiperazine; alkyl, e.g., $C_1$–$C_2$ alkyl, ethylenediamines, e.g., N-ethylethylenediamine, N,N-dimethylethylenediamine, N,N'-dimethylethylenediamine, N,N-diethylethylenediamine, N,N'-diethylethylenediamine, N,N-dimethyl-N'-ethylethylenediamine, and N,N,N',N'-tetramethylethylenediamine; propylenediamines, e.g., 1,2-propylenediamine, and 1,3-propylenediamine; alkyl, e.g, $C_1$–$C_3$ alkyl, propylenediamines, e.g., N-methyl-1,3-propylenediamine; alkanolamines, e.g., mono-, di- and tri (2-hydroxyethyl)amine; alkylamino alkanols, e.g., $C_1$–$C_6$ alkylamino $C_1$–$C_{12}$ alkanols, e.g., 2-(ethylamino)ethanol, and 2-(diethylamino)ethanol; $C_5$–$C_7$ cycloaliphatic amines, e.g., cyclohexylamine, N-methylcyclohexylamine, and 1,4-diazobicyclo[2.2.2]octane; and aromatic amines, e.g., aniline, N-ethylaniline, and N,N-diethylaniline.

As used herein, the term "ethyleneamine" is meant to refer to one or more amines belonging to the family of ethyleneamines as previously recited. In a preferred embodiment of the present invention, the amine hydrohalide is an amine hydrochloride, and the amine of the amine hydrochloride is selected from the group consisting of ammonia, monoalkylamines, dialkylamines, trialkylamines, ethyleneamines, alkyl ethylenediamines, propylenediamines, alkyl propylenediamines, monoalkanolamines, dialkanolamines, trialkanolamines, cycloaliphatic amines, aromatic amines, and mixtures of such amines, as described previously. In a particularly preferred embodiment of the present invention, the amine of the amine hydrochloride is an "ethyleneamine" and is selected from the group consisting of ethylenediamine, diethylenetriamine, triethylenetetramine, tetraethylenepentamine, pentaethylenehexamine, piperazine, 1-(2-aminoethyl)piperazine, and mixtures of such ethyleneamines.

The operation of electrolytic cells 5 and 2 of FIGS. 1 through 4 will now be described as it relates to preferred embodiments of the process of the present invention. An aqueous solution of amine hydrohalide is circulated through catholyte compartment 13 by forwarding the solution from a source of amine hydrohalide, e.g., temperature controlled reservoir 60 shown in FIGS. 2 and 3, through a suitable conduit (shown by line 37); introducing the solution into catholyte compartment 13 through inlet 49; withdrawing a process stream comprising free amine and amine hydrohalide from catholyte compartment 13 through outlet 53; and forwarding that process stream by a suitable conduit (shown by line 39) to the source of amine hydrohalide, e.g., reservoir 60.

Figure 2:
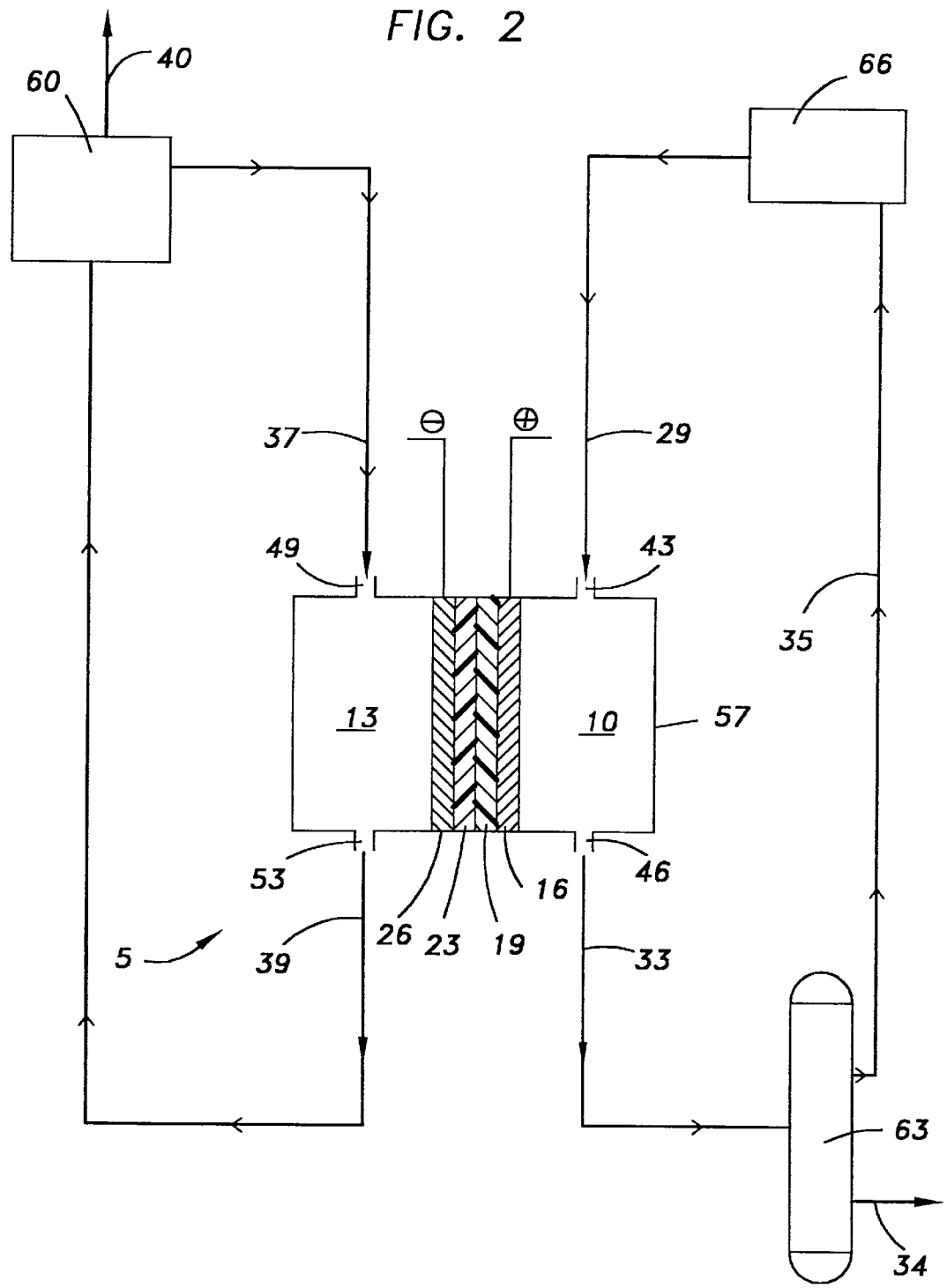
FIG. 2 is a schematic of the electrolytic cell depicted in FIG. 1 further comprising closed loops around the catholyte and anode compartments for the process streams charged to and withdrawn from such compartments, and means for removing and recovering concentrated, substantially dry hydrogen halide from the anode compartment.
Figure 3:
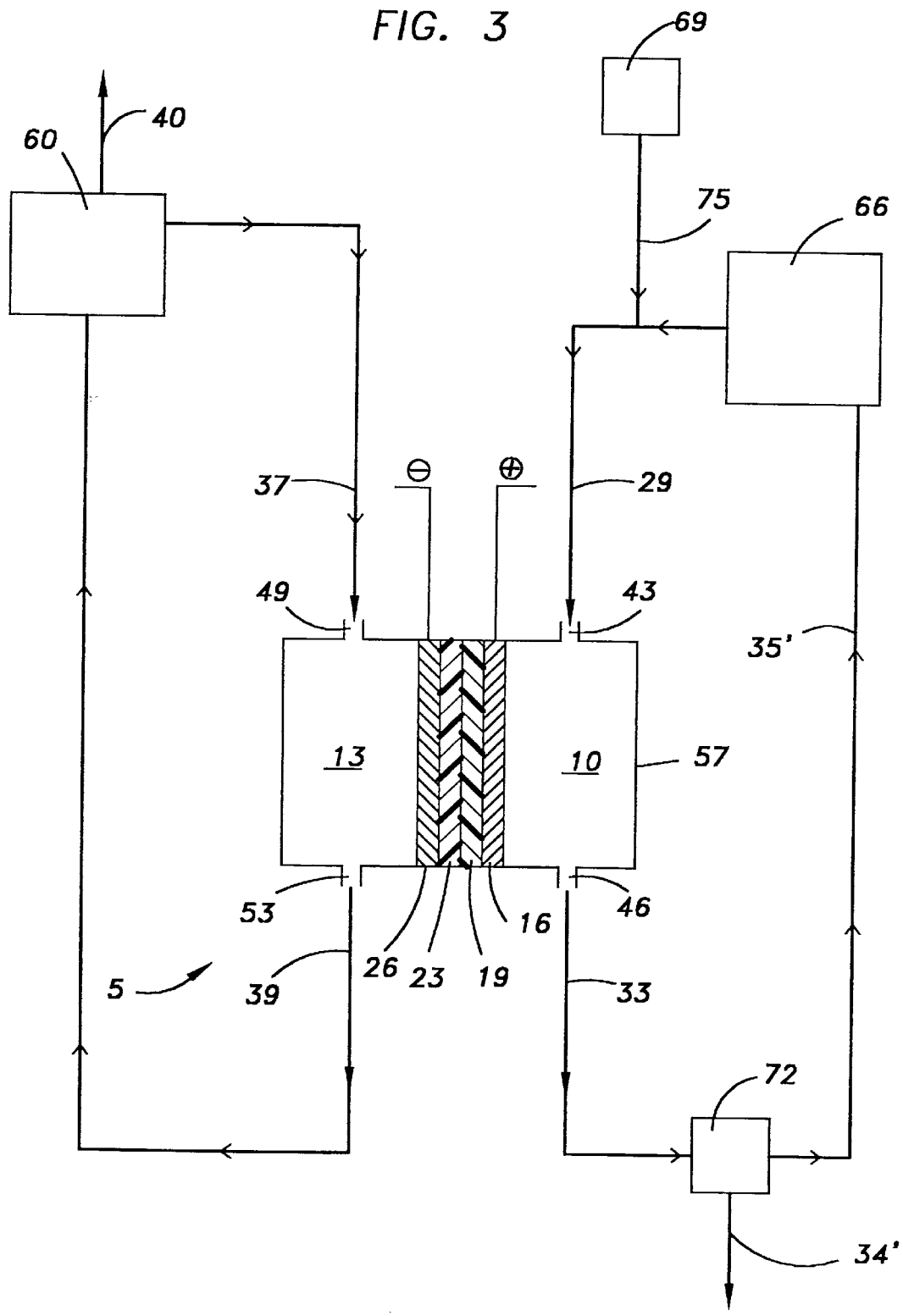
FIG. 3 is a schematic of the electrolytic cell depicted in FIG. 1 further comprising closed loops around the catholyte and anode compartments for the process streams charged to and withdrawn from such compartments, and means for introducing steam into, and recovering concentrated aqueous hydrogen halide from, the anode compartment.

Similarly and simultaneously, in connection with electrolytic cell 5, hydrogen gas is circulated through anode compartment 10 by forwarding hydrogen gas from a source of hydrogen, e.g., reservoir 66 shown in FIGS. 2 and 3, through a suitable conduit or transfer line (shown by line 29); introducing such hydrogen gas into anode compartment 10 through inlet 43; withdrawing hydrogen gas from the anode compartment 10 through outlet 46; and forwarding withdrawn hydrogen gas by a suitable conduit or transfer line (shown by line 33) to the source of hydrogen, e.g., reservoir 66.

In connection with electrolytic cell 2 of FIG. 4, a hydrogen gas-containing aqueous solution is circulated through anode compartment 10 by forwarding said hydrogen gas-containing solution, from a reservoir, not shown, to anode compartment 10 through a suitable conduit (shown by line 29'); introducing such hydrogen gas-containing solution into the anode compartment 10 through inlet 43; withdrawing hydrogen gas-containing solution from anode compartment 10 through outlet 46; and forwarding withdrawn hydrogen gas-containing solution through a conduit or transfer line (shown by line 33') to the source of source of hydrogen gas-containing solution, e.g., a reservoir not shown. The hydrogen gas-containing aqueous solution is preferably comprised of water and hydrogen gas. Other gas(es) may be present with the hydrogen gas circulated through the anode compartment 10., e.g., nitrogen, as long as such other gas(es) does not adversely affect the operation of the electrolytic cell. In particular, it is preferred that the hydrogen gas-containing stream be substantially free of carbon monoxide (CO) as carbon monoxide can poison or otherwise degrade the gas diffusion hydrogen gas anode 19 of eletrolytic cell 5, and the porous catalytic particles 11 of electrolytic cell 2 of FIG. 4.

The temperature at which the aqueous solution of amine hydrohalide is maintained depends on, for example, its boiling point and the operating temperature limits of the anion exchange membrane. In the practice of the present invention, the aqueous solution of amine hydrohalide is typically maintained at a minimum temperature of at least 25° C., preferably at least 30° C., and more preferably at least 40° C. The aqueous solution of amine hydrohalide is also typically maintained at a maximum temperature of less than 70° C., preferably less than 65° C., and more preferably less than 60° C. The temperature at which the aqueous solution of amine hydrohalide is maintained may range between any combination of these minimum and maximum temperature values, inclusive of the recited values.

The aqueous solution of amine hydrohalide typically contains amine hydrohalide present in an amount of at least 5% by weight, preferably at least 10% by weight, and more preferably at least 25% by weight, based on the total weight of the aqueous solution of amine hydrohalide. The aqueous solution of amine hydrohalide also typically contains amine hydrohalide present in an amount of not more than 50% by weight, preferably not more than 40% by weight, and more preferably not more than 35% by weight, based on the total weight of the aqueous solution of amine hydrohalide. The amount of amine hydrohalide present in the aqueous solution of amine hydrohalide may range between any combination of these amounts, inclusive of the recited amounts.

In accordance with the method of the present invention, direct current is passed through the electrolytic cell while the aforedescribed process streams are circulated through the catholyte and anode compartments. Electrolytic cells 5 and 2 may be operated at a current density of at least 0.05 Kiloamperes per square meter of electrode surface available for electrochemical reaction (Kamps/m$^2$), preferably at least 0.1 Kamps/m$^2$, and more preferably at least 0.2 Kamps/m$^2$. The current density also may be not more than 10 Kamps/m$^2$, preferably not more than 7 Kamps/m$^2$, and more preferably not more than 6 Kamps/m$^2$. In the practice of the method of the present invention, the current density may range between any combination of these values, inclusive of the recited values. The surface area of the electrode being here calculated from its perimeter dimensions alone.

While not meaning to be bound by any theory, it is believed from the evidence at hand that the current passing through the electrolytic cell results in the following chemical and electrochemical reactions. The electrochemical and chemical reactions believed to occur within the catholyte compartment 13 may be represented by the following General Scheme I:

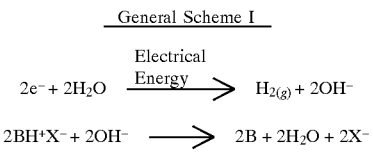

General Scheme I $$2e^- + 2H_2O \xrightarrow{\text{Electrical Energy}} H_{2(g)} + 2OH^-$$

$$2BH^+X^- + 2OH^- \longrightarrow 2B + 2H_2O + 2X^-$$

wherein BH$^+$X$^-$ represents an amine hydrohalide, X$^-$ represents a halide anion, and B represents free amine. The halide anion X$^-$ is selectively transported across anion exchange membrane 23 and passes into hydrogen consuming gas diffusion anode 19. The electrons consumed, as shown in General Scheme I, are provided by cathode 26.

Within anode compartment 10, the following electrochemical and chemical reactions are believed to occur, as represented by General Scheme II:

General Scheme II

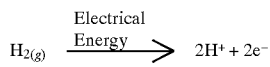

Within and/or on the surface of the hydrogen consuming gas diffusion anode 19 of electrolytic cell 5, the halide anion $X^-$ together with the hydrogen cation $H^+$ forms gaseous hydrogen halide. The electrons produced, as shown in General Scheme II, are transferred by electrical contact from the hydrogen consuming gas diffusion anode 19 to the current collecting electrode 16.

In the case of electrolytic cell 2, within and/or on the surface of catalytic particles 11, the halide anion together with the hydrogen cation forms hydrogen halide which dissolves in the aqueous medium to form aqueous hydrogen halide. The electrons produced are likewise transferred to the current collecting electrode 16 directly from the bed of porous catalytic particles 11 and/or through the aqueous solution circulating through the anode compartment.

During the operation of either of electrolytic cells 5 or 2, the concentration of free amine within the circulating aqueous solution of amine hydrohalide increases with each pass through catholyte compartment 13. The process stream withdrawn from catholyte compartment 13 will contain a higher amount of free amine than the process stream entering catholyte compartment 13. Correspondingly, the process stream withdrawn from anode compartment 10 will contain a higher amount of hydrogen halide than the process stream entering anode compartment 10.

When the concentration of free amine in the process stream circulating through catholyte compartment 13 reaches a desired level, the free amine is recovered from that stream. The aqueous solution from which the free amine is recovered will typically contain an amount of free amine that is at least 50 percent greater than that of the aqueous solution of amine hydrohalide initially charged to catholyte compartment 13. Of the total molar equivalents of amine hydrohalide initially present in the aqueous solution of amine hydrohalide circulated through catholyte compartment 13, at least 50%, preferably at least 80%, and more preferably at least 95% of these equivalents are converted to free amine in accordance with the practice of the method of the present invention.

While a batch process has been described, a continuous process for converting the amine hydrohalide to free amine is contemplated. For example, a side stream of the circulating aqueous stream of amine hydrohalide can be removed to make the process a continuous or semi-continuous process.

In one contemplated embodiment of the present invention, electrolytic cells 5 and 2 are operated until 95% to 99.5%, and preferably 98% to 99.5% of the total molar equivalents of amine hydrohalide initially present in the aqueous solution of amine hydrohalide circulated through catholyte compartment 13 are converted to free amine. To convert the remaining, e.g., 0.5% to 5%, molar equivalents of unconverted amine hydrohalide to free amine, the aqueous solution comprising free amine removed from catholyte compartment 13 may be treated with a small amount of alkali metal hydroxide, e.g., sodium hydroxide, followed by separation of the resulting alkali metal halide salt, e.g., sodium chloride.

In a modification of the above embodiment, the remaining, e.g., 0.5% to 5%, molar equivalents of unconverted amine hydrohalide are converted to free amine by passing the aqueous solution comprising free amine removed from catholyte compartment 13 through an ion exchange resin, which is contained in one or more ion exchange columns. For example, the removed aqueous solution comprising free amine containing from for example 0.5% to 5% molar equivalents of unconverted amine hydrohalide, based on the total equivalents of amine hydrohalide initially present in the aqueous solution of amine hydrohalide, is passed through an anion exchange column or a series of anion exchange columns containing anion exchange resins, which exchange hydroxide anions ($OH^-$) for halide anions ($X^-$). The hydroxide anions released from the column(s) serve to convert the amine cation ($BH^+$) to free amine (B) and water.

Ion exchange columns useful in the aforedescribed finishing process, are well known and typically are filled with a solid sorbant material comprised of a porous water insoluble synthetic organic polymer having acidic or basic groups along the polymer backbone (ion exchange resin). Cation exchange resins have acidic groups, while anion exchange resins have basic groups, along the polymer backbone. Examples of suitable organic polymers from which the sorbant material may be comprised include, but are not limited to, phenolic based polymers, styrene based polymers and acrylic based polymers. A general illustrative example of an anion exchange resin is polystyrene having either quaternary ammonium groups or tertiary amine groups covalently bonded to at least some of the benzene rings of the polystyrene backbone. An example of a commercially available anion exchange resin useful in the practice of the present invention is AMBERJET® 4400 OH resin, from Rohm and Hass Company.

In accordance with the embodiment of the present invention described with reference to FIG. 2, hydrogen halide gas is recovered as concentrated substantially dry hydrogen halide from the hydrogen gas stream removed from anode compartment 10. By concentrated substantially dry hydrogen halide is meant hydrogen halide having less than 2% by weight of water, preferably less than 1% by weight of water, and more preferably less than 0.5% by weight of water, based on the total weight of the concentrated substantially dry hydrogen halide collected. The concentrated substantially dry hydrogen halide, e.g., hydrogen chloride, can be recovered by forwarding the hydrogen gas process stream containing hydrogen halide removed from anode compartment 10 (or a portion thereof) to condenser 63. In condenser 63, the hydrogen halide gas condenses as concentrated substantially dry hydrogen halide; is separated from the circulating hydrogen gas; and withdrawn from the condenser by means of conduit 34. The hydrogen gas stream removed from condenser 63 through conduit 35 is substantially free of hydrogen halide and is recycled to reservoir 66. By substantially free of hydrogen halide is meant that the hydrogen gas stream in conduit 35 contains less than 0.5% by weight of hydrogen halide, based on the total weight of the hydrogen gas stream 35.

In addition, hydrogen gas generated in catholyte compartment 13 can be removed from reservoir 60 through conduit 40. The hydrogen gas removed from conduit 40 may be transferred to hydrogen gas reservoir 66 by way of a conduit not shown.

In accordance with the embodiment of the present invention described with reference to FIG. 3, steam from steam source 69 is introduced into anode compartment 10 by adding it to conduit 29 by means of conduit 75, which connects the steam source with conduit 29. The steam serves to enhance the removal of hydrogen halide, e.g., hydrogen chloride, from the surface of the hydrogen consuming gas diffusion anode 19. The hydrogen halide is dissolved in the steam and is withdrawn from anode compartment 10 as concentrated aqueous hydrogen halide. By concentrated aqueous hydrogen halide is meant an aqueous solution of hydrogen halide having present therein from 25% to 35% by weight of hydrogen halide, preferably from 28% to 35% by weight of hydrogen halide, and more preferably from 30% to 35% by weight of hydrogen halide, based on the total weight of the concentrated aqueous hydrogen halide collected. The concentrated aqueous hydrogen halide is forwarded to hydrogen halide collection unit 72 through conduit 33, and removed therefrom through conduit 34'. The hydrogen gas removed from concentrated aqueous hydrogen halide collection unit 72 and forwarded to reservoir 66 through conduit 35' is substantially free of hydrogen halide. By substantially free of hydrogen halide is meant that the hydrogen gas in conduit 35' contains less than 0.5% by weight of hydrogen halide, based on the total weight of the hydrogen gas stream passing through conduit 35'.

While FIGS. 1–4 depict singular representations of electrolytic cells, it should be understood that the scope of the present invention is also inclusive of the utilization of a plurality of such cells. The present invention may be practiced using a plurality of cells, e.g., electrolytic cells 5 or 2, either in series or parallel. In one embodiment, a plurality of cells, not shown, e.g., electrolytic cell 5, are utilized in series, wherein outlets 53 and 46 of each preceding cell are in respective communication with inlets 49 and 43 of each succeeding cell by means of additional conduits, not shown.

In another embodiment of the present invention, a plurality of cells, not shown, e.g., electrolytic cell 5, are utilized in parallel, wherein inlet 49 and outlet 53 of catholyte compartment 13 of each cell are in common closed loop communication with reservoir 60 by means of conduits and manifolds, not shown. Accordingly, inlet 43 and outlet 46 of anode compartment 10 of each cell are in common closed loop communication with reservoir 66 by means of conduits and manifolds, not shown.

The present invention is more particularly described in the following example, which is intended to be illustrative only, since numerous modifications and variations therein will be apparent to those skilled in the art. Unless otherwise specified, all parts and percentages are by weight.

EXAMPLE

An electrolytic cell, as represented in FIG. 1, was constructed of poly(vinylidenefluoride). The catholyte and anode compartments each had an active electrode area of 10 centimeters (cm)×10 cm available for electrochemical reaction. The cathode and the current collecting electrodes were each constructed in a mesh-like configuration of platinum coated titanium. A NEOSEPTA® ACM anion exchange membrane, available from Tokuyama Soda of Japan, was used. The hydrogen consuming gas diffusion anode was comprised of 95% by weight of platinum supported on hydrophilic carbon black, and 5% by weight of TEFLON® polytetrafluoroethylene polymer having a platinum per surface area value of 4 milligrams (mg)/cm$^2$. The hydrogen consuming gas diffusion anode was hot pressed onto the NEOSEPTA® ACM anion exchange membrane.

An aqueous solution of 10% by weight, based on the total weight of aqueous solution, of ethylenediamine dihydrochloride was circulated at a rate of 180 milliliters (ml)/minute through the catholyte compartment from a temperature controlled stainless steel reservoir pressurized to 0.35 Kg/cm$^2$ gauge (5 pounds per square inch gauge (psig)), using a fluid metering pump. The contents of the stainless steel reservoir were maintained at a temperature of from 40° C. to 50° C. The flow of hydrogen gas through the anode compartment was maintained at a rate of 300 ml/minute using a mass flow controller. Steam was also passed through the anode compartment to facilitate the removal of hydrogen chloride from the surface of the hydrogen consuming gas diffusion anode. The outlet of the anode compartment was attached to a water-filled hydrogen chloride scrubber having a back pressure of 305 mm (12 inches) of water. The electrolytic cell was equipped with devices for measuring temperature, and a power source having voltage and current control, and a coulomb counter. The electrolytic cell was operated at a current density of 0.3 Kamps/m$^2$, and samples were withdrawn from the catholyte compartment at various intervals, as indicated in Table 1.

TABLE 1

| Time Sample Taken[a] (minutes) | 0 | 90 | 127 |
|---|---|---|---|
| Total Charge Consumed[b] (coulombs) | 0 | 16,620 | 26,500 |
| Free Ethylenediamine[c] (mg/g) | 6.79 | 8.49 | 9.53 |
| % Current Efficiency[d] | N.A.[1] | 97.9 | 97.8 |

[1]N.A. = Not Applicable.
[a]Samples were withdrawn directly from the catholyte chamber. The times shown are cumulative and represent the total time that the electrolytic cell was operated at 3 amps.
[b]Total Charge Consumed was determined by taking readings from the coulomb counter. The values shown are cumulative.
[c]The cumulative amount of free ethylenediamine (EDA) detected in the samples withdrawn from the catholyte chamber, and is given in units of milligrams of free EDA per gram of sample withdrawn, (mg/g). Just prior to withdrawing a sample, the current being supplied to the electrolytic cell was turned off. After removing a sample, the current was again applied to the electrolytic cell. The amount of free EDA was determined by acid titration using a standard HCl solution.
[d]% Current Efficiency determined by the following equation: 100 × (actual free EDA produced in the catholyte compartment / theory free EDA that could have been produced in the catholyte compartment). The actual free EDA produced was determined as described above. The theory free EDA produced was determined by calculation using the Faraday equation and the measured amount of charge consumed.

The results summarized in Table 1 show the high current efficiency which can be achieved in the electrochemical preparation of free 1,2-ethylenediamine from 1,2-ethylenediamine dihydrochloride according to the practice of the present invention.

The present invention has been described with reference to specific details of particular embodiments thereof. It is not intended that such details be regarded as limitations upon the scope of the invention except insofar as and to the extent that they are included in the accompanying claims.

We claim:

1. A method of converting amine hydrohalide into free amine comprising:

(a) providing an electrolytic cell having a catholyte compartment containing a cathode; and an anode compartment containing an anode assembly, said anode assembly comprising a hydrogen consuming gas diffusion anode fixedly held between a current collecting electrode and an anion exchange membrane; said catholyte and anode compartments being separated by said anion exchange membrane;

(b) introducing an aqueous solution of amine hydrohalide into said catholyte compartment;

(c) introducing hydrogen gas into said anode compartment;

(d) passing direct current through said electrolytic cell; and (e) removing an aqueous solution comprising free amine from said catholyte compartment.

2. The method of claim 1 wherein the amine hydrohalide is an amine hydrochloride.

3. The method of claim 2 wherein the amine of the amine hydrochloride is selected from the group consisting of ammonia, monoalkylamines, dialkylamines, trialkylamines, ethyleneamines, alkyl ethylenediamines, propylenediamines, alkyl propylenediamines, monoalkanolamines, dialkanolamines, trialkanolamines, cycloaliphatic amines, aromatic amines, and mixtures thereof.

4. The method of claim 3 wherein the amine of the amine hydrochloride is an ethyleneamine which is selected from the group consisting of ethylenediamine, diethylenetriamine, triethylenetetramine, tetraethylenepentamine, pentaethylenehexamine, piperazine, 1-(2-aminoethyl)piperazine, and mixtures thereof.

5. The method of claim 1 further comprising the step of removing a hydrogen halide-containing hydrogen gas stream from said anode compartment and recovering substantially dry hydrogen halide from said gas stream.

6. The method of claim 1 further comprising introducing steam into said anode compartment.

7. The method of claim 6 further comprising the step of removing aqueous hydrogen halide from said anode compartment.

8. The method of claim 1 wherein a positive internal pressure difference of from 0.07 $Kg/cm^2$ to 1.40 $Kg/cm^2$ exists between said catholyte and anode compartments.

9. The method of claim 1 wherein said hydrogen consuming gas diffusion anode comprises platinum supported on carbon black dispersed in polytetrafluoroethylene.

10. The method of claim 9 wherein said anion exchange membrane comprises a copolymer of styrene and divinylbenzene having pendent quaternary ammonium salt groups.

11. The method of claim 10 wherein said cathode and said current collecting electrode each comprises a material selected from the group consisting of graphite, platinum, titanium coated with platinum, titanium coated with an oxide of ruthenium, nickel, stainless steel, high alloy steel and appropriate combinations thereof.

12. The method of claim 1 further comprising the step of passing aqueous solution comprising free amine removed from said catholyte compartment through an anion exchange resin.

13. The method of claim 1 wherein said hydrogen consuming gas diffusion anode comprises platinum supported on carbon black dispersed in polytetrafluoroethylene, said anion exchange membrane comprises a styrene-divinylbenzene copolymer having pendent quaternary ammonium salt groups; and said amine hydrohalide is amine hydrochloride.

14. The method of claim 13 wherein the amine of the amine hydrochloride is an ethyleneamine which is selected from the group consisting of ethylenediamine, diethylenetriamine, triethylenetetramine, tetraethylenepentamine, pentaethylenehexamine, piperazine, 1-(2-aminoethyl)piperazine, and mixtures thereof.

15. The method of claim 14 wherein said cathode and said current collecting electrode are each comprised of a material selected from the group consisting of graphite, platinum, titanium coated with platinum, titanium coated with an oxide of ruthenium, nickel, stainless steel, high alloy steel and appropriate combinations thereof.

16. The method of claim 15 further comprising introducing steam into said anode compartment.

17. The method of claim 16 further comprising removing aqueous hydrogen chloride from said anode compartment.

18. The method of claim 17 wherein a positive internal pressure difference of from 0.07 Kg/cm to 1.40 $Kg/cm^2$ exists between said catholyte and anode compartments.

19. The method of claim 13 further comprising removing a hydrogen chloride-containing hydrogen gas stream from said anode compartment and recovering substantially dry hydrogen chloride from said gas stream.

20. The method of claim 13 further comprising passing aqueous solution comprising free amine removed from said catholyte compartment through an anion exchange resin.

21. A method of converting amine hydrohalide into free amine comprising:

(a) providing an electrolytic cell having a catholyte compartment containing a cathode; and an anode compartment containing an anode assembly, said anode assembly comprising an anion exchange membrane, a current collecting electrode, and a bed of porous catalytic particles; said catholyte and anode compartments being separated by said anion exchange membrane;

(b) introducing an aqueous solution of amine hydrohalide into said catholyte compartment;

(c) introducing a hydrogen gas-containing aqueous solution into said anode compartment;

(d) passing direct current through said electrolytic cell; and (e) removing an aqueous solution comprising free amine from said catholyte compartment.

22. The method of claim 21 wherein the porous catalytic particles are comprised of a substrate substantially coated with an admixture of a hydrophobic binder and a catalyst material selected from the group consisting of platinum, ruthenium, osmium, rhenium, rhodium, iridium, palladium, tungsten carbide, gold, titanium, zirconium and combinations thereof, said substrate being selected from the group consisting of steel, iron, graphite, nickel, platinum, copper and silver.

23. The method of claim 22 wherein said substrate is graphite, said hydrophobic binder is polytetrafluoroethylene, and said catalyst material is platinum supported on carbon black.

24. The method of claim 21 wherein said anion exchange membrane comprises a copolymer of styrene and divinylbenzene having pendent quaternary ammonium salt groups.

25. The method of claim 21 wherein said cathode and said current collecting electrode are each comprised of a material selected from the group consisting of graphite, platinum, titanium coated with platinum, titanium coated with an oxide of ruthenium, nickel, stainless steel, high alloy steel, and appropriate combinations thereof.

26. The method of claim 21 further comprising passing aqueous solution comprising free amine removed from said catholyte compartment through an anion exchange resin.

* * * * *